United States Patent
Makino

(10) Patent No.: US 9,157,892 B2
(45) Date of Patent: Oct. 13, 2015

(54) SURFACE PROPERTY INSPECTION DEVICE AND SURFACE PROPERTY INSPECTION METHOD

(75) Inventor: Yoshiyasu Makino, Toyokawa (JP)

(73) Assignee: SINTOKOGIO, LTD., Aichi (JP)

(*) Notice: Subject to any disclaimer, the term of this patent is extended or adjusted under 35 U.S.C. 154(b) by 174 days.

(21) Appl. No.: 14/116,313

(22) PCT Filed: May 9, 2012

(86) PCT No.: PCT/JP2012/062442
§ 371 (c)(1),
(2), (4) Date: Nov. 7, 2013

(87) PCT Pub. No.: WO2012/153862
PCT Pub. Date: Nov. 15, 2012

(65) Prior Publication Data
US 2014/0084910 A1 Mar. 27, 2014

(30) Foreign Application Priority Data

May 10, 2011 (JP) .................................. 2011-104965

(51) Int. Cl.
*G01N 27/80* (2006.01)
*G01N 27/82* (2006.01)
*G01B 7/06* (2006.01)
*G01N 27/90* (2006.01)

(52) U.S. Cl.
CPC ............... *G01N 27/82* (2013.01); *G01B 7/105* (2013.01); *G01N 27/80* (2013.01); *G01N 27/9046* (2013.01)

(58) Field of Classification Search
CPC .................................................... G01N 27/80
USPC ......................................................... 324/243
See application file for complete search history.

(56) References Cited

U.S. PATENT DOCUMENTS

| 5,485,084 | A | 1/1996 | Duncan et al. |
| 2008/0001609 | A1 | 1/2008 | Kojima et al. |

FOREIGN PATENT DOCUMENTS

| DE | 2259113 A1 | 6/1974 |
| EP | 0 135 204 A2 | 3/1985 |

(Continued)

OTHER PUBLICATIONS

International Search Report for International Application No. PCT/JP2012/062442, dated Jul. 31, 2012, 2 pages.

*Primary Examiner* — Bot Ledynh
(74) *Attorney, Agent, or Firm* — Brinks Gilson & Lione

(57) ABSTRACT

To provide a surface property inspection device and surface property inspection method with which the surface treatment condition of treated material such as steel subjected to such surface treatments as shot-peening treatment or heat treatment, nitriding, and the like can be non-destructively and precisely inspected, and which offers a high degree of general purpose application. A surface property inspection device 1 includes an AC power supply, an AC bridge circuit, and a judgment device, and the AC bridge circuit has a variable resistor with a variable split ratio γ, a benchmark detector, and an inspection detector. In variable resistor setting step S1, the split ratio γ of a variable resistor is adjusted and set so that the output from the AC bridge circuit is increased; after setting a frequency at which the output from the AC bridge circuit is maximized using a frequency setting step S2, in pass/fail judgment step S4, a benchmark sample S is brought into contact with the benchmark detector, the sample under inspection M is brought into contact with the inspection detector, and the output from the LPF 33 and the threshold value set in the threshold value setting step S3 are compared and a pass/fail judgment is made of the surface condition of the sample under inspection M.

14 Claims, 5 Drawing Sheets

(56) References Cited

FOREIGN PATENT DOCUMENTS

| | | |
|---|---|---|
| JP | 62-142258 A | 6/1987 |
| JP | 62-147356 A | 7/1987 |
| JP | 01-254857 A | 10/1989 |
| JP | 4-66863 A | 3/1992 |
| JP | 7-92140 A | 4/1995 |
| JP | 2008-002973 A | 1/2008 |
| JP | 2009-168556 A | 7/2009 |

SURFACE PROPERTY INSPECTION DEVICE AND SURFACE PROPERTY INSPECTION METHOD

This application is a 371 application of PCT/JP2012/062442 having an international filing date of May 9, 2012 which claims priority to JP2011-104965 filed May 10, 2011, the entire contents of which are incorporated herein by reference.

TECHNICAL FIELD

The present invention pertains to a surface property inspection device and surface property inspection method for making a non-destructive pass/fail inspection of the surface treatment condition of processed material subjected to surface processing such as shot-peening or heat treatment, nitriding, or the like.

BACKGROUND ART

Surface treatments such as surface hardening by heat treatment, nitriding, and the like, or shot peening, are performed on gears, shafts, or other steel products used in automobile parts and the like to improve wear-resistance, fatigue strength, etc.

Conventionally, evaluation of surface properties such as residual stress, hardness, and the like following surface treatment of these parts was done by sample destructive testing. This led to the problem that not all products could therefore not be directly tested, and because testing was destructive, tested products became unusable.

There is therefore an increasing need to develop a device capable of non-destructive testing of product surface properties. Patent Document 1, for example, discloses a non-destructive inspection device for shot-preened surfaces wherein an AC (Alternating Current) signal is input as frequency is varied to an inspection circuit furnished with a coil, disposed above a shot-peening treatment surface, and frequency response characteristics of the impedance in that test circuit are used to inspect the state of residual stress in the object under inspection.

Patent Document 1: JP-A-2008-2973

SUMMARY OF THE INVENTION

Problems the Invention Seeks to Resolve

However, elements of magnetic measurements such as magnetic permeability and electrical conductivity, which change under surface treatment, are affected by environmental changes, therefore in the device set forth in JP-A-2008-2973, the problem arises that measurement errors tend to occur when the environment in which a benchmark sample is measured differs from the environment in which a sample under inspection is inspected.

In a surface treatment surface inspection method using the frequency response characteristics of impedance, impedance of the detector and the sample under inspection changes relative to changes in the frequency of the power applied for measurement, making it difficult to detect with accuracy electromagnetic changes arising from the surface treatment condition of the sample under inspection.

In the AC power applied for measurement, the frequency at which sensitivity increases for detecting pass/fail for a sample under inspection changes depending on the material and surface treatment condition of the sample under inspection. Therefore in a measurement device furnished with only one detector, it is necessary to first measure output values relative to changes in frequency for a surface treated part and an untreated part, and select the optimal frequency at which the difference between the output value for the surface treated part and that for the untreated part is at a maximum. This raises the problem that time and labor must be expended on the work of selecting frequencies.

When the shape, material properties, and surface treatment method of a sample under inspection differ, the detection circuit should be designed to adapt to changes in the overall impedance of the detector. Moreover, it is also necessary to calibrate the residual stress distribution relative to the impedance value, such that the device does not have high general purpose application.

The present invention therefore has the object of providing a surface property inspection device and surface property inspection method with which the surface treatment condition of treated material such as steel subjected to surface treatments such as shot-peening treatment or heat treatment, nitriding, and the like can be non-destructively and precisely inspected, and offering a high degree of general purpose application.

Means for Resolving the Problem

To accomplish the above, the invention of Claim 1 comprising: an AC bridge circuit; an AC power supply for supplying AC power to the AC bridge circuit; and a judgment device for making a pass/fail judgment of the surface treatment condition of a sample under inspection based on the output signal from the AC bridge circuit; wherein the AC bridge circuit includes a variable resistor constituted so that the split ratio between a first resistor and a second resistor is variable, a benchmark detector having a first magnetic sensor for detecting the magnetic properties of a benchmark sample in a good surface treatment condition, and an inspection detector having a second magnetic sensor for detecting the magnetic properties of a sample under inspection for which a pass/fail inspection of the surface treatment condition is to be made; and the first resistor, the second resistor, the benchmark detector, and the inspection detector constitute a bridge circuit; and wherein the judgment device judges the pass/fail status of the surface treatment condition of the sample under inspection based on the output signal from the AC bridge circuit in a state in which AC power is supplied to the AC bridge circuit, the first magnetic sensor detects the magnetic properties of the benchmark sample, and the second magnetic sensor detects the magnetic properties of the sample under inspection.

In the invention set forth in Claim 1, a pass/fail judgment of the surface treatment condition of the sample under inspection is made by the judgment device based on the output signal output from the AC bridge circuit, therefore the surface treatment condition of the sample under inspection can be inspected in the same measurement environment while constantly comparing to the benchmark sample, thereby enabling a highly accurate inspection of surface state using a simple circuit configuration. By adopting the AC bridge circuit configuration, it is unnecessary to correct for temperature, obtain test data based on the material of the sample under inspection, or calibrate device output relative to residual stress distribution, etc. And since the split ratio of the variable resistor is variable, the circuit does not have to be redesigned even if the impedance of the benchmark detector or the inspection detector changes.

Therefore a surface property inspection device can be realized with which the surface treatment condition of treated material such as steel subjected to such surface treatments as shot-peening or heat treatment, nitriding, and the like can be non-destructively and precisely inspected, and a high degree of general purpose application is afforded.

In the invention set forth in Claim 2, the surface property inspection device of Claim 1 is further furnished with a frequency adjuster for adjusting and setting the frequency of AC power supplied from the AC power supply.

In the invention set forth in Claim 2, the frequency of the AC power supplied from the AC power supply can be adjusted, therefore broader impedance changes to the benchmark detector and the inspection detector can be handled.

The invention set forth in Claim 3, whereby in the surface property inspection device of Claim 2, is constituted wherein in a state in which the first magnetic sensor detects the magnetic properties of the benchmark sample, and the second magnetic sensor detects the magnetic properties of a non-surface treated sample or a reference sample which is a sample in a poor surface treatment condition, the frequency is set by the frequency adjuster so that the amplitude of the output signal from the AC bridge circuit increases.

The invention set forth in Claim 3 is constituted to vary the frequency of the AC power supplied to the AC bridge circuit by the frequency adjuster and set a frequency at which the amplitude of the signal output from the AC bridge circuit increases, therefore the frequency at which the output from the AC bridge circuit increases can be set by a single operation in response to samples under inspection in which the surface treatment condition and shape differ and impedance changes. Output therefore responds sensitively to changes in surface treatment condition, and inspection sensitivity can be improved.

The invention set forth in Claim 4, whereby in the surface property inspection device of Claim 3, is constituted wherein in a state in which the first magnetic sensor detects the magnetic properties of the benchmark sample, and the second magnetic sensor detects the magnetic properties of a non-surface treated sample or a reference sample which is a sample in a poor surface treatment condition, the split ratio of the variable resistor is set so that the amplitude of the output signal from the AC bridge circuit increases.

In the invention set forth in Claim 4, by constituting the two sides of the AC bridge circuit as variable resistors with variable split ratios, the split ratio is adjusted so that the output from the AC bridge circuit is increased and set to enable inspection under appropriate conditions, thus permitting an expansion of the range of types of inspected piece and surface treatment to which the surface property inspection device can be applied, and providing a device with a high degree of general purpose application, capable of handling multiple types of detectors.

In the invention set forth in Claim 5, the surface property inspection device of Claim 4 is further furnished with a phase comparator for detecting the phase difference between the AC power waveform supplied from the AC power supply and the output signal waveform from the AC bridge circuit, and wherein the judgment device makes a pass/fail judgment as to whether the inspection is being favorably conducted, based on the phase difference detected by the phase comparator.

Using the invention set forth in Claim 5, phase differences between the AC power supplied from the power supply and the AC bridge circuit output can be detected by the phase comparator. By monitoring this phase difference, a judgment can be made as to whether the inspection state is good or bad. For example, if the phase difference changes greatly even when the output from the AC bridge circuit is the same, a judgment can be made that there is a risk that a change in inspection state may have occurred.

In the invention set forth in Claim 6, the first and second magnetic sensors in the surface property inspection device of Claim 5 are respectively furnished with a core formed of a magnetic body and a coil wound on this core, and the second magnetic sensor detects the electromagnetic properties of the sample under inspection by supplying AC power from the AC power supply to the coil to form a closed magnetic path to the core and the surface of the sample under inspection.

In the invention set forth in Claim 6, the cores of the first and second magnetic sensors and the surface of the sample under inspection form a closed magnetic path, thereby enabling the prevention of attenuation or leakage of magnetism between the sample under inspection and the magnetic sensor. Detection sensitivity of electromagnetic properties by the benchmark detector and the inspection detector can thus be improved, and the detection sensitivity of electromagnetic properties is improved in accordance with surface treatment condition, therefore the surface treatment condition of a sample under inspection can be nondestructively and accurately evaluated.

In the invention set forth in Claim 7, the surface property inspection device of Claim 6 further has a sample under inspection placement device for adjusting the location and pressure load at which the sample under inspection is brought into contact with the second magnetic sensor.

In the invention set forth in Claim 7, the position at which each sample is brought into contact with each magnetic sensor and the pressure loads thereon can be adjusted in essentially the same way, therefore the contact conditions between each sample and each magnetic sensor can be made uniform, and detection accuracy improved.

The invention set forth in Claim 8 is a surface property inspection method, comprising steps of: a preparation step for providing an AC bridge circuit and an AC power supply for supplying AC power to the AC bridge circuit; the AC bridge circuit comprising a variable resistor constituted so that the split ratio between a first resistor and a second resistor is variable, a benchmark detector including a first magnetic sensor for detecting the magnetic properties of a benchmark sample in a good surface treatment condition, and an inspection detector including a second magnetic sensor for detecting the magnetic properties of a sample under inspection for which a pass/fail determination of surface treatment condition is to be made, and the first resistor, the second resistor, the benchmark detector and the inspection detector constituting a bridge circuit; a sample placement step for placing the benchmark sample in contact or proximity with the first magnetic sensor and for placing the sample under inspection in contact or proximity with the second magnetic sensor so that magnetic properties are detected; an AC supply step for supplying AC power to the AC bridge circuit from the AC power supply; and a pass/fail judgment step for making a pass/fail judgment of the surface treatment condition of the sample under inspection based on an output signal output from the AC bridge circuit.

In the invention set forth in Claim 8, a pass/fail judgment of the surface treatment condition of the sample under inspection is made based on the signal output from the AC bridge circuit, therefore the surface treatment condition of the sample under inspection can be inspected in the same measurement environment while constantly comparing to the benchmark sample, thereby enabling a highly accurate inspection of surface state using a simple circuit configuration. By adopting the AC bridge circuit configuration, corrections for temperature, obtaining of test data based on the material of the sample under inspection, and calibration of device output relative to residual stress distribution, etc. become unnecessary.

Since the split ratio of the variable resistor is variable, the circuit does not have to be redesigned even if the impedance of the benchmark detector or the inspection detector changes.

Therefore a surface property inspection method can be realized with which the surface treatment condition of treated material such as steel subjected to such surface treatments as shot-peening or heat treatment, nitriding, and the like can be non-destructively and precisely inspected, and a high degree of general purpose application is afforded.

The invention set forth in Claim 9, whereby the surface property inspection method of Claim 8, is further furnished with a frequency setting step for setting the frequency so that the amplitude of the signal output from the AC bridge circuit increases when the frequency of the AC power supplied from the AC power supply is varied, in a state in which the first magnetic sensor detects magnetic properties of the benchmark sample and the second magnetic sensor detects magnetic properties of a non-surface treated sample, or of a reference sample which is a sample in a poor surface treatment condition; and in the AC supply step, AC power is supplied at the frequency set in the frequency setting step.

In the invention set forth in Claim 9, by varying the frequency of the AC power supplied to the AC bridge circuit to set a frequency at which the amplitude of the voltage output from the AC bridge circuit increases, the frequency at which the output from the AC bridge circuit increases can be set by a single operation in response to samples under inspection in which the surface treatment condition or shape differ so that impedance differs. Output therefore responds sensitively to changes in surface treatment condition, and inspection sensitivity can be improved.

The invention set forth in Claim 10, whereby the surface property inspection method of Claim 9, is further furnished with a variable resistor setting step for determining a split ratio by adjusting the variable resistor so that output is increased in a state in which the first magnetic sensor detects magnetic properties of the benchmark sample and the second magnetic sensor detects magnetic properties of a non-surface treated sample, or of a reference sample which is a sample in a poor surface treatment condition; and in the AC supply step, the variable resistor is set to achieve the split ratio determined in the variable resistor setting step.

In the invention set forth in Claim 10, by constituting the two sides of the AC bridge circuit as variable resistors with a variable split ratio, the split ratio can be adjusted so that the output from the AC bridge circuit is increased and set to enable inspection under appropriate conditions, thus permitting an expansion of the range of the types of inspected piece and surface treatment inspectable with the surface property inspection device, and providing a device with a high degree of general purpose application, capable of handling multiple types of detectors.

In the invention set forth in Claim 11, the surface property inspection method of Claim 10 is further furnished with a threshold setting step for determining a threshold value for making a pass/fail judgment based on the output signal from the AC bridge circuit in a state in which the first magnetic sensor detects magnetic properties of the benchmark sample and the second magnetic sensor detects magnetic properties of a non-surface treated sample or of a reference sample which is a sample in a poor surface treatment condition, and based on the output signal from the AC bridge circuit in a state in which the first and second magnetic sensors respectively detect magnetic properties of the benchmark sample; and in the pass/fail judgment step, a pass/fail judgment of the surface treatment condition of the sample under inspection is made based on the threshold value.

In the invention set forth in Claim 11, in a state whereby the second magnetic sensor detects magnetic properties of the benchmark sample and the reference sample, threshold values can be respectively set based on the respective output signals output from the AC bridge circuit and used for a pass/fail judgment of the surface treatment condition of the sample under inspection in the pass/fail judgment step.

In the invention set forth in Claim 12, the surface property inspection method of Claim 11 is further furnished with an inspection state judgment step for detecting phase differences between the AC power waveform supplied from the AC power supply and the AC bridge circuit output signal waveform to make a pass/fail judgment of the inspection state based on detected phase differences.

In the invention set forth in Claim 12, the inspection state judgment step detects phase differences between the AC power waveform supplied from the AC power supply and the signal waveform output from the AC bridge circuit, and is able to make a pass/fail judgment of the inspection state based on the detected phase differences. For example, if the phase difference changes greatly even when the output from the AC bridge circuit is the same, a judgment can be made of a risk that a change in inspection state may have occurred.

In the invention set forth in Claim 13, the first and second magnetic sensors in the surface property inspection method of Claim 12 are respectively furnished with a core formed of a magnetic body and a coil wound on this core, and the second magnetic sensor detects the electromagnetic properties of the sample under inspection by supplying AC power from the AC power supply to the coil to form a closed magnetic path to the core and the surface of the sample under inspection.

In the invention set forth in Claim 13, the cores of the first and second magnetic sensors and the surface of the sample under inspection form a closed magnetic path, thereby enabling prevention of attenuation or leakage of magnetism between the sample under inspection and the magnetic sensor. Detection sensitivity of electromagnetic properties by the benchmark detector and the inspection detector can thus be improved, and the detection sensitivity of electromagnetic properties is improved in accordance with surface treatment condition, therefore the surface treatment condition of a sample under inspection can be nondestructively and accurately evaluated.

The invention set forth in Claim 14 is the surface property inspection method of Claim 13, wherein in the sample placement step the pressure load for bringing the first magnetic sensor into contact with the benchmark sample and the pressure load for bringing the second magnetic sensor into contact with the sample under inspection are set to be approximately the same.

In the invention set forth in Claim 14, the pressure loads for bringing each sample into contact with each magnetic sensor are approximately the same, and the contact conditions between each sample and each magnetic sensor can be made uniform, therefore detection accuracy is improved.

DETAILED DESCRIPTION OF THE PREFERRED EMBODIMENTS

Figure 1:
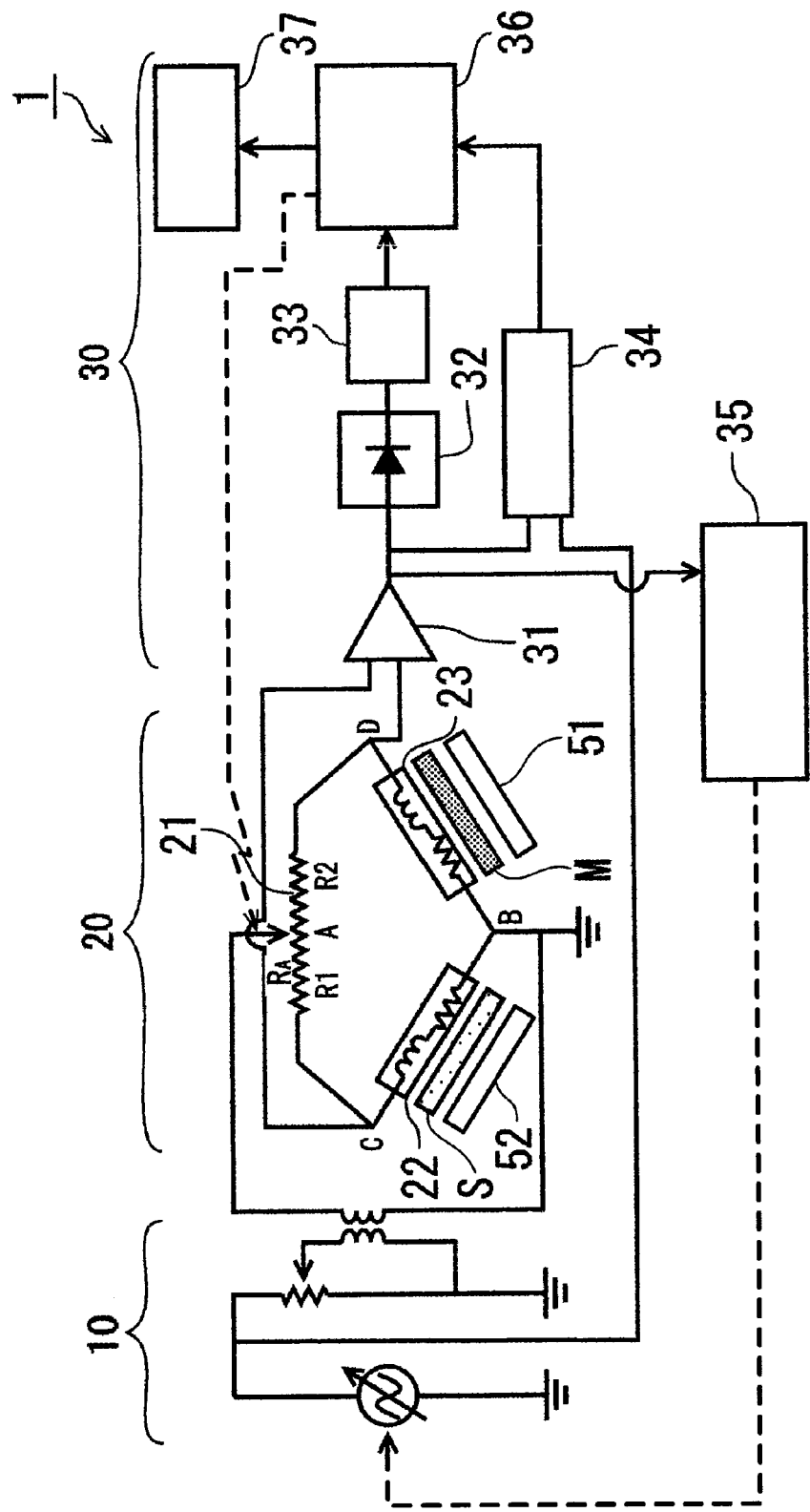
FIG. 1: An explanatory figure showing the circuit configuration in a surface property inspection device according to an embodiment of the present invention.

As shown in FIG. 1, the surface property inspection device 1 according to an embodiment of the present invention is furnished with an AC power supply 10, an AC bridge circuit 20, and a judgment device 30.

The AC power supply 10 is capable of supplying variable frequency AC power to the AC bridge circuit 20.

The AC bridge circuit 20 is furnished with a variable resistor 21, a benchmark detector 22 provided with a magnetic sensor for detecting the magnetic properties of a benchmark sample S, and an inspection detector 23 provided with a magnetic sensor for detecting magnetic properties of a sample under inspection M.

The variable resistor 21 is capable of variably splitting a resistance $R_A$ between resistors R1 and R2 in a split ratio γ. The resistors R1 and R2 form a bridge circuit together with the benchmark detector 22 and the inspection detector 23. In the present embodiment, the point A splitting resistor R1 and resistor R2, and point B between the benchmark detector 22 and the inspection detector 23 are connected to the AC power supply 10 of the judgment device 30, and the point C between the resistor R1 and the benchmark detector 22 and point D between the resistor R2 and the inspection detector 23 are connected to the amplifier 31. To reduce noise, the side of the benchmark detector 22 and inspection detector 23 is grounded.

The judgment device 30 is furnished with an amplifier 31 for amplifying the voltage signal output from the AC bridge circuit 20, an absolute value circuit 32 for performing full-wave rectification, a low-pass filter 33 (LPF) for DC conversion, a phase comparator 34 for comparing phases of the AC voltage supplied from the AC power supply 10 and the voltage output from the amplifier 31, a frequency adjustment device 35 for adjusting the frequency of the AC voltage supplied from the AC power supply 10, a judgment means 36 for making a pass/fail judgment of the surface condition of the sample under inspection M based on the output from the LPF 33, and a display means 37 for displaying and giving warning of the judgment results by the judgment means 36.

The amplifier 31 is connected to points C and D, and the electric potential difference between points C and D is input thereto. Also, the absolute value circuit 32 and LPF 33 are connected in sequence to the judgment means 36. The phase comparator 34 is connected to the AC power supply 10, the amplifier 31, and the judgment means 36. The frequency adjustment device 35 is connected to the AC power supply 10 and the amplifier 31. The judgment means 36 is constituted to be able, by outputting a control signal, to change the position of point A in the AC bridge circuit 20, i.e., to change the resistor R1 and resistor R2 split ratio γ, and thereby to execute the variable resistor setting step described below.

Figure 2:
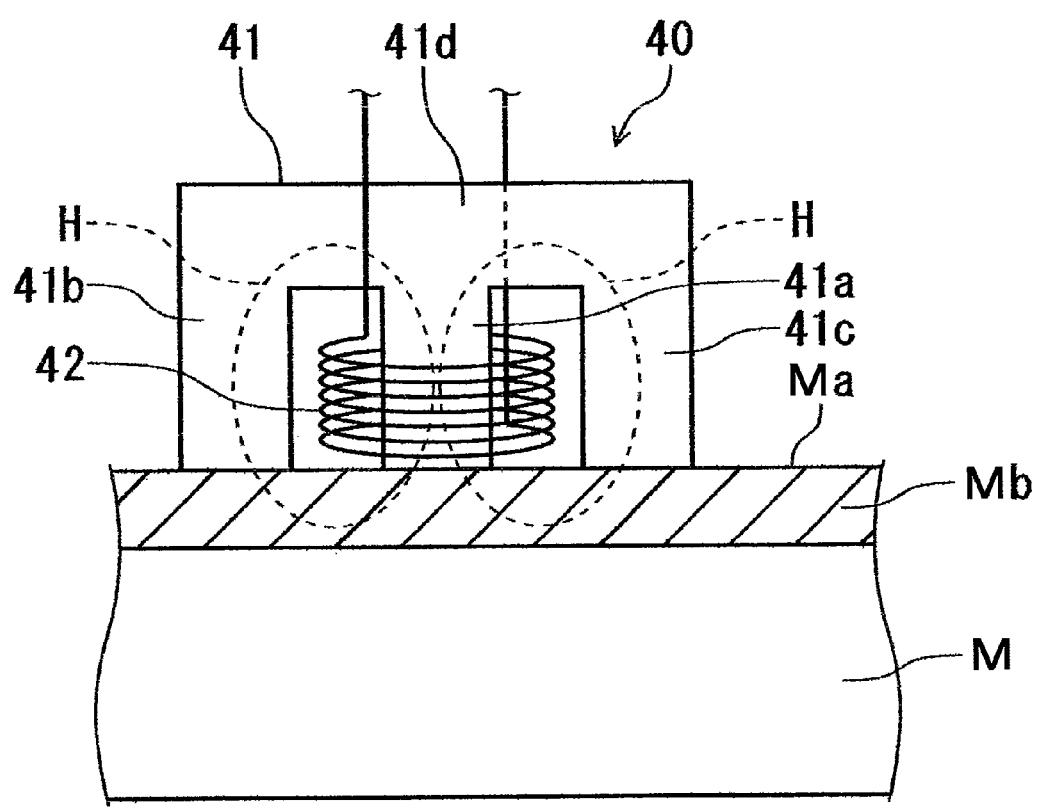
FIG. 2: An explanatory figure showing an example of a magnetic sensor.

A magnetic sensor shaped to form a closed magnetic path by bringing a magnetic sensor into contact or proximity with the surface of a sample under inspection is used as the magnetic sensor constituting the benchmark detector 22 and the inspection detector 23. In the present embodiment, as shown in FIG. 2, a magnetic sensor provided with an E-shaped core is adopted.

The magnetic sensor 40 comprises an E-shaped core 41 formed of a magnetic body, in which a foot portion 41a, and feet portions 41b and 41c, disposed on both flanks of the foot portion 41a are protruded from the base portion 41d toward the surface Ma of the sample under inspection M to form an E; and a coil 42 wound on the foot portion 41a.

Here, the core 41 is formed by a magnetic body, a high magnetic flux density is created inside the core 41 and the S/N ratio (S: magnetism penetrating steel material; N: leakage magnetism) can be increased, enabling an improvement in the magnetic detection sensitivity of the magnetic sensor, which is desirable. Examples of strongly magnetic bodies include iron, super permalloy, permalloy, silicon steel, ferrite (Mn—Zn based and Ni—Zn based), carbonyl iron dust, molybdenum permalloy, sendust, and the like.

In the magnetic sensor 40, the end portions of the feet portions 41a, 41b, and 41c are respectively formed to be capable of contacting the surface of a sample under inspection M. For example, when the sample under inspection M is flat, the tip portions of the feet portions 41a, 41b, and 41c are formed to lie on the same plane, and the magnetic sensor 40 is disposed so that the feet portions 41a, 41b, and 41c respectively come into contact with the surface of the sample under inspection M.

Note that the surface property inspection device 1 of the present embodiment is furnished with a benchmark sample placement device 51 for placing so that the benchmark sample S is brought into contact with the magnetic sensor of the benchmark detector 22, and a sample under inspection placement device 52 for placing so that the sample under inspection M is brought into contact with the magnetic sensor of the inspection detector 23 (FIG. 1).

We now discuss an example in which the sample under inspection M is steel, on which a residual stress layer Mb is formed by shot-peening. When AC power is supplied at a predetermined frequency from the AC power supply 10 to the coil 42, an AC magnetic field H is generated at the core 41; magnetism penetrates to a predetermined depth of the residual stress layer Mb on the sample under inspection M according to frequency, and a closed magnetic path is formed by the feet portions 41a, 41c and the region to a predetermined depth in the residual stress layer Mb on the sample under inspection M.

The AC magnetic field H passing through the coil 12 changes according to the electromagnetic properties of the residual stress layer Mb into which magnetism penetrates, therefore the impedance of the coil 42 changes according to properties (surface treatment condition) of the residual stress layer Mb. Hence magnetic properties of the residual stress layer Mb can be detected by the coil 42.

Magnetic attenuation or leakage between the sample under inspection M and the magnetic sensor 40 is preferably prevented by disposing the magnetic sensor 40 to contact the surface Ma of the sample under inspection M. By this means, detection sensitivity to magnetic properties responsive to surface treatment condition improves, thus enabling the surface treatment condition of samples under inspection to be non-destructively and accurately evaluated. Liftoff-caused fluctuation errors can also be reduced.

Note that when a closed magnetic path is formed by the magnetic sensor 40 and the surface of the sample under inspection M (the residual stress layer Mb), and a sufficiently large voltage is output from the AC bridge circuit 20, it is not necessary to cause the magnetic sensor 40 to come into contact with the sample under inspection M surface Ma; it is sufficient to bring them into proximity.

Figure 3:
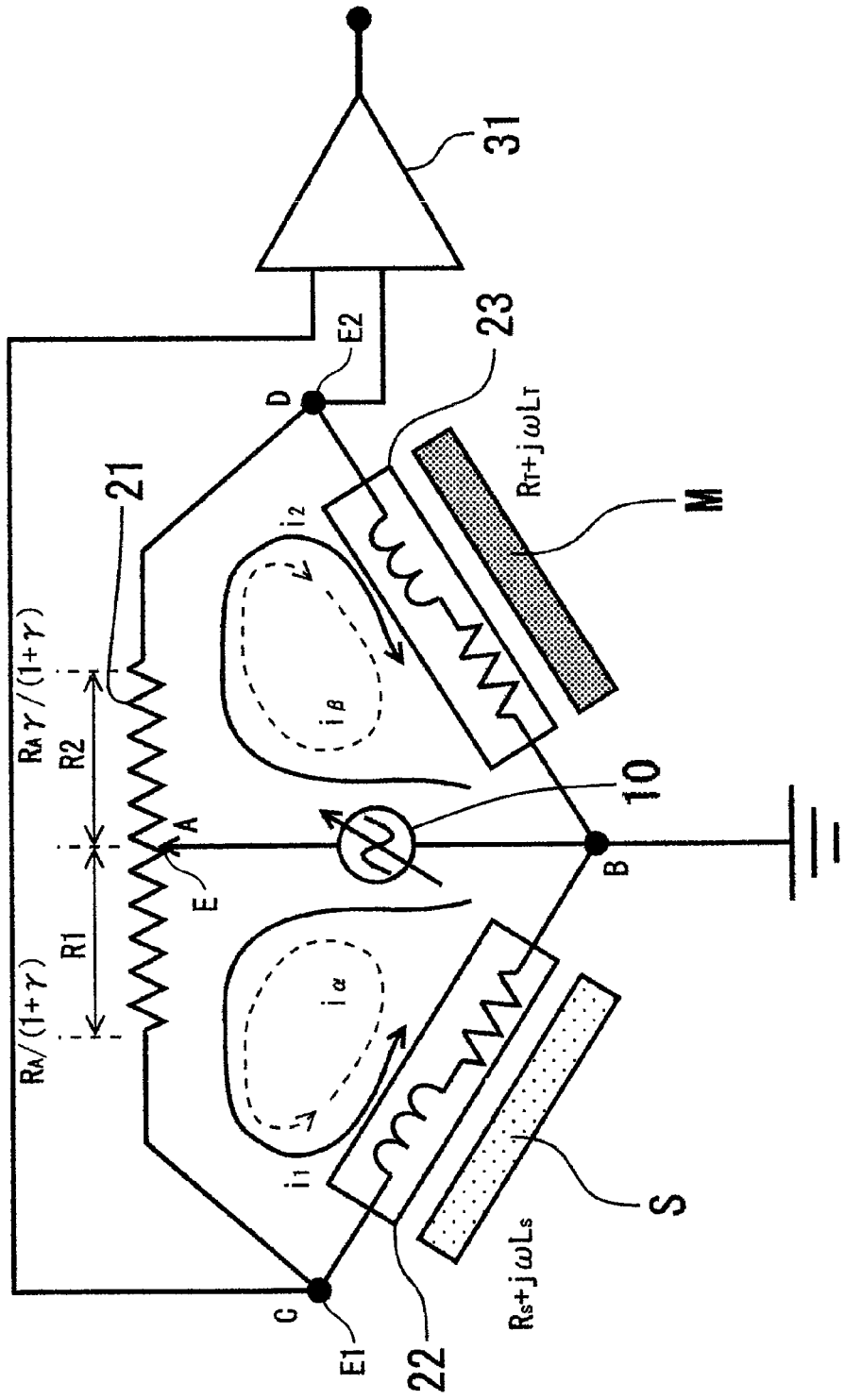
FIG. 3: An equivalent circuit diagram explaining the output from an AC bridge circuit.

Next, referring to the FIG. 3 equivalent circuit, we discuss the output from the AC bridge circuit 20, adjusted to a non-equilibrium state. Benchmark sample S, for which the surface treatment condition is guaranteed good, is brought into contact with the benchmark detector 22, and the sample under inspection M for which a surface treatment condition pass/fail is to be determined is brought into contact with the inspection detector 23.

When the variable resistor $R_A$ split ratio is γ, the resistor R1 is $R_A/(1+\gamma)$ and the resistor R2 is $R_A\gamma(1+\gamma)$. Benchmark detector 22 impedance is assumed to be $R_S+j\omega L_S$, and the impedance of the inspection detector 23 is assumed to be $R_T+j\omega L_T$. E is the potential at point A, $i_1$, $i_2$ are the respective excitation currents flowing at each edge of the bridge when each of the samples (benchmark sample S, sample under inspection M) is not brought into contact with the benchmark detector 22 or the inspection detector 23, and iα and iβ are the respective currents flowing in response to the amount of change in magnetism caused by bringing each of the samples into contact with the benchmark detector 22 and the inspection detector 23. The potentials E1 and E2 and excitation currents $i_1$, and $i_2$ on the benchmark detector 22 and inspection detector 23 in this instance are expressed by Equations (1) through (4) below.

Expression 1

$$E1 = (R_S + j\omega L_S)(i\alpha + i_1) \quad (1)$$

Expression 2

$$E2 = (R_T + j\omega L_T)(i\beta + i_2) \quad (2)$$

Expression 3

$$i_1 = \frac{E}{\frac{R_A}{1+\gamma} + R_S + j\omega L_S} \quad (3)$$

Expression 4

$$i_2 = \frac{E}{\frac{R_A\gamma}{1+\gamma} + R_T + j\omega L_T} \quad (4)$$

The voltage output on the amplifier 31 is the differential between E1 and E2, and is expressed by the following formula:

Expression 5

$$E2-E1=[\{(R_T+j\omega L_T)i\beta-(R_S+j\omega L_S)i\alpha\}+\{(R_T+j\omega L_T)i_2-(R_S+j\omega L_S)i_1\}] \quad (5)$$

The following expression is derived from Expressions (3) through (5):

Expression 6

$$E2-E1 = \left[\left\{\left(R_T + j\omega L_T\right)i\beta - (R_S + j\omega L_S)i\alpha\right\} + \left\{(R_T + j\omega L_T)\frac{E}{\frac{R_A\gamma}{1+\gamma} + R_T + j\omega L_T} - (R_S + j\omega L_S)\frac{E}{\frac{R_A}{1+\gamma} + R_S + j\omega L_S}\right\}\right] \quad (6)$$

The right hand side of Expression (6) can be divided into the following components A and B to consider each of the components of the differential voltage.

$$(R_T + j\omega L_T)i\beta - (R_S + j\omega L_S)i\alpha \quad \text{Component A}$$

$$(R_T + j\omega L_T)\frac{E}{\frac{R_A\gamma}{1+\gamma} + R_T + j\omega L_T} - \quad \text{Component B}$$

$$(R_S + j\omega L_S)\frac{E}{\frac{R_A}{1+\gamma} + R_S + j\omega L_S}$$

Component A is comprised of each of the detector components: $(R_S+j\omega L_S)$, $(R_T+j\omega L_T)$, and the amount of current change when each sample is brought into contact with each detector is comprised of iα and iβ. The size of iα and iβ varies according to the amount of magnetism passing through the sample due to magnetic properties of each sample, such as magnetic permeability and conductivity. It is therefore possible to change iα and iβ by changing the excitation currents $i_1$ and $i_2$ which control the amount of magnetism produced by each detector. It can also be seen from Expressions (3) and (4) that excitation currents $i_1$ and $i_2$ change depending on the variable resistor split ratio γ, therefore the size of component A can be changed by adjusting the variable resistor split ratio γ.

Component B is comprised of each of the detector components: $(R_S+j\omega L_S)$, $(R_T+j\omega L_T)$, and the resistance parameter spit by the variable resistor split ratio γ. Therefore as with component A, the size of the component B can be changed by adjusting the variable resistor split ratio γ.

Figure 4:
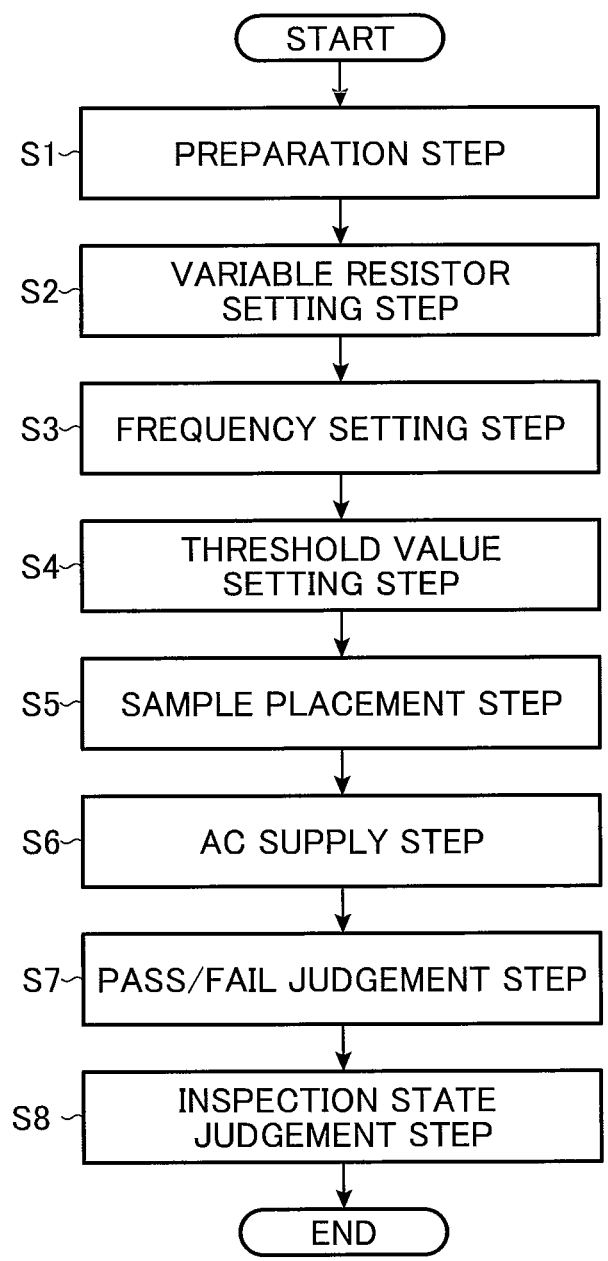
FIG. 4: A flow chart showing a surface property inspection method.

Next, referring to FIG. 4, we discuss a method for inspecting the surface properties of a sample under inspection using a surface property inspection device 1.

First, in preparation step S1, a surface property inspection device 1 according to an embodiment of the present invention is prepared. A benchmark sample of guaranteed good surface treatment condition and a reference sample, which is a sample not subjected to surface treatment or a sample with a poor surface treatment condition, are also prepared.

Next, in variable resistor setting step S2, the benchmark sample S is brought into contact with the benchmark detector 22, and the reference sample is brought into contact with the inspection detector 23. Here, in order to improve inspection accuracy, it is preferable to match the contact conditions between each sample and each detector. In the embodiment, the positional relationship and the pressure load between the benchmark sample S and the benchmark detector 22 is set by the benchmark sample placement device 51, and the positional relationship and the pressure load between the reference sample or the sample under inspection M and the inspection detector 23 is set by the sample under inspection placement device 52. The benchmark sample placement device 51 and sample under inspection placement device 52 are set so that the positional relationship and the pressure load between each sample and each detector is approximately the same. Note that in the present embodiment the benchmark sample placement device 51 and the sample under inspection placement device 52 are constituted by a position-adjustable XY stage on which each sample is loaded, and by a load weight adjustment device for effecting a fixed pressure load. The load weight adjustment device comprises a combination of a micrometer and a known mechanism which spins when a fixed load is applied. Moreover, because the benchmark detector 22 and inspection detector 23 are disposed in close proximity, these detectors may be placed in the same installation environment, so that they are less affected even if temperature, humidity, or surrounding electromagnetic environment change.

Next, AC power is supplied from the AC power supply 10 to the AC bridge circuit 20. In this state, the split ratio γ of the variable resistor 21 is adjusted so that detection sensitivity to bad samples by the surface property inspection device 1 is increased. I.e., in a state whereby the benchmark sample S is pressed onto the benchmark detector 22, and the reference sample is pressed onto the inspection detector 23, the split ratio γ on the variable resistor 21 is adjusted so that a large output signal is output from the AC bridge circuit 20. By thus setting the variable resistor 21, the difference in output signal increases between the case when the sample under inspection M pressed onto the inspection detector 23 has a poor surface treatment condition, and the case in which the surface treatment condition is good, enabling an improvement in detection accuracy. Specifically, the voltage amplitude of the output signal from the AC bridge circuit 20, or the voltage output from the LPF 33, is monitored on a display device with a waveform display function such as an oscilloscope (e.g., provided on the judgment means 36), and the split ratio γ is adjusted so output is increased. The split ratio γ of the variable resistor 21 is preferably adjusted and set so that the output has a maximum value or local maximum value (local equilibrium point).

Adjustment of the split ratio γ on the variable resistor 21 is accomplished by increasing the output difference in response to differences in surface condition by raising the differential voltage (E2−E1), thereby improving inspection accuracy. As described above, since components A and B are changed by adjusting the split ratio γ, the split ratio γ of the variable resistor 21 can be adjusted according to benchmark detector 22 and inspection detector 23 impedances $(R_S+j\omega L_S)$, $(R_T+j\omega L_T)$ to increase the differential voltage (E2−E1), which is the output from the AC bridge circuit 20, and thereby improve inspection accuracy.

In the frequency setting step S3, with the benchmark sample S brought into contact with the benchmark detector 22 and the reference sample brought into contact with the inspection detector 23, AC power is supplied from the AC power supply 10 to the AC bridge circuit 20, and the frequency of the AC power supplied to the AC bridge circuit 20 is changed by the frequency adjustment device 35 as the voltage amplitude output from the AC bridge circuit 20 or the voltage output from the LPF 33 is monitored.

The frequency adjustment device 35 outputs a control signal to the AC power supply 10 to establish the initial frequency f1 set in the frequency adjustment device 35, and the output voltage Ef1 from the amplifier 31 at frequency f1 is input to the frequency adjustment device 35 and stored. Next, a control signal is output to the AC power supply 10 so that the frequency goes to f2, which is higher by a predetermined value—e.g. 100 Hz—than the frequency f1; an output voltage Ef2 from the amplifier 31 at frequency f2 is input to the frequency adjustment device 35 and stored.

Next, a comparison is made between Ef1 and Ef2; if Ef2>Ef1, a control signal is output so that the frequency goes to f3, which is higher by a predetermined value than frequency f2, and an output voltage Ef3 output from the amplifier 31 at frequency f3 is input to the frequency adjustment device 35 and stored. Ef2 and Ef3 are then compared. This is repeated, and the frequency fn when Efn+1<Efn, which is to say the frequency fn at which output is largest, is set as the frequency used in the threshold setting step S4 and the AC supply step S6. The frequency to increase output from the AC bridge circuit 20 in response to samples under inspection M with differing surface treatment conditions, shape, etc. and therefore differing impedances, can thus be set by a single operation. While optimum frequency does change according to the material, shape, and surface treatment condition of the sample under inspection, there is no need to set a frequency when this is known in advance. Output therefore responds sensitively to changes in surface treatment condition, and inspection sensitivity can be improved.

Here the frequency setting step S3 is executed before the variable resistor setting step S2.

In the threshold setting step S4, the benchmark sample S is brought into contact with the benchmark detector 22, the benchmark sample S or reference sample is brought into contact with the inspection detector 23, and AC power at the frequency set in frequency setting step S3 is supplied from the AC power supply 10 to the AC bridge circuit 20. The voltage output from the AC bridge circuit 20 is amplified by the amplifier 31 and full-wave rectified by the absolute value circuit 32; a DC conversion is performed by LPF 33 and output to the judgment means 36.

The output value output to the judgment means 36 when the benchmark sample S is brought into contact with the inspection detector 23 is set as the normal threshold value, and the output value output to the judgment means 36 when the reference sample is brought into contact with the inspection detector 23 is set as the bad threshold value; these are stored in the judgment means 36.

In the relationship between surface treatment condition and electromagnetic properties, magnetic permeability is reduced, for example, when a compound layer is formed. Permeability also rises when the surface hardens. Magnetic permeability drops due to the inverse magnetostriction effect when a compressive residual stress has been imparted by shot-peening treatment or the like. The bad threshold value varies from the normal threshold value according to differences in magnetic permeability.

In the pass/fail judgment step (S7), the output value and the normal threshold value and bad threshold value are compared when the sample under inspection M is brought into contact with the inspection detector 23, and a pass/fail judgment about the sample under inspection M is made. When the set good threshold value is greater than the bad threshold value, the product is judged to be good when the output value from the sample under inspection M is equal to or greater than the normal threshold value, and the product is judged to be bad when the output value of the sample under inspection M is equal to or less than the bad threshold value.

Note that depending on the type of sample under inspection, etc., it can occur that the bad threshold value is greater than the normal threshold value. In such cases, the product is judged to be good when the output value from the sample under inspection M is equal to or less than the normal threshold value, and the product is judged to be bad when the output value of the sample under inspection M is equal to or greater than the bad threshold value.

When making a pass/fail judgment of a sample under inspection M as described above, pass/fail determination can be made when the output value of the sample under inspection M is a value between the normal threshold value and the bad threshold value. An output measurement is made using multiple reference samples of differing surface conditions; the bad threshold value can also be set to reduce the difference relative to the normal threshold value. The bad threshold value may also be more precisely determined by a concurrent destructive inspection of the sample under inspection.

In the sample placement step S5, the sample under inspection M, for which a pass/fail determination is to be made of the surface treatment condition, is brought into contact with the inspection detector 23. Note that the benchmark detector 22 is in a state whereby it is contacted by the benchmark sample S, which was brought into contact in threshold setting step S4.

Next, in AC supply step S6, AC power at the frequency set in frequency setting step S3 is supplied from the AC power supply 10 to the AC bridge circuit 20. As a result of AC power being supplied to the AC bridge circuit 20, a voltage output signal is supplied from the AC bridge circuit 20. This output signal is amplified by the amplifier 31, full-wave rectified by the absolute value circuit 32, and converted to DC by the LPF 33.

In pass/fail judgment step S7, the signal converted to DC in LPF 33 is input to the judgment means 36, and the judgment means 36 makes a pass/fail judgment of the surface condition of the sample under inspection M based on the input signal. Judgment results by the judgment means 36 are displayed by the display means 37, and a warning is issued when the surface condition is a bad.

The judgment of pass/fail of the surface treatment condition of the sample under inspection M is made by comparing the output value (measurement value) from the LPF 33 with the normal threshold value and the bad threshold value set in threshold setting step S4.

In the inspection condition judgment step S8, the waveform of the AC power supplied from the AC power supply 10 and the AC voltage waveform output from the AC bridge circuit 20 are compared by the phase comparator 34, and the phase difference between them is detected. By monitoring this phase difference, a judgment can be made as to whether the inspection state is good or bad. For example, it can occur that if the state of contact of the inspection detector 23 with the sample under inspection M differs and lift-off between the detector and the sample under inspection changes, phase will shift. Therefore even when the output from the AC bridge circuit 20 is the same, changes occur in the inspection state when the phase difference changes greatly, so that a judgment can be made that the inspection may not have been correctly performed.

The steps above enable a simple and highly accurate inspection of whether the surface treatment condition of the sample under inspection M is good or bad. To continue the inspection, only the sample under inspection M is exchanged, and it is sufficient to repeat the sample placement step S5, AC supply step S6, pass/fail judgment step S7, and inspection condition judgment step S8. Variable resistor setting step S2, frequency setting step S3, and threshold setting step S4 are again executed when the type of sample under inspection M, type of surface treatment, etc. are changed.

Here, by changing the variable resistor 21 split ratio γ, the range of types of inspectable samples under inspection, types of surface treatment, and the like can be broadened. For example, when inspecting samples under inspection M of differing materials, the above-described iα and iβ change, and the differential voltage (E2−E1) changes. By adjusting the split ratio γ in variable resistor setting step S1 and setting so that the differential voltage (E2−E1) is increased according to the material of the sample under inspection M, each respective sample under inspection M of differing material can be inspected in an appropriate state.

In the surface property inspection device 1, multiple types of benchmark detector 22 and inspection detector 23 suited to forming a closed magnetic path according to the size and shape of the sample under inspection M, are preferably prepared and exchanged and used according to the sample under inspection M.

Here impedance differs in each detector, but since the split ratio can be adjusted in the variable resistor setting step S1 and set so that the differential voltage (E2−E1) increases according to detector impedance, inspection in an appropriate state is possible for each of multiple detectors.

As described above, by constituting the two sides of the AC bridge circuit 20 by a variable resistor 21 with a variable a split ratio γ, the differential voltage (E2−E1) can be adjusted, therefore the surface property inspection device 1 can be a device with high general purpose application, capable of handling multiple detectors and samples under inspection.

In this circuit configuration, the split ratio γ can be adjusted to create a large difference in the proportions of excitation currents $i_1$ and $i_2$ flowing in the benchmark detector 22 and inspection detector 23, enabling a greater increase in component A, which is caused by the electromagnetic properties of the sample under inspection M and is necessary for inspection of the surface treatment condition.

Variant Example

Figure 5:
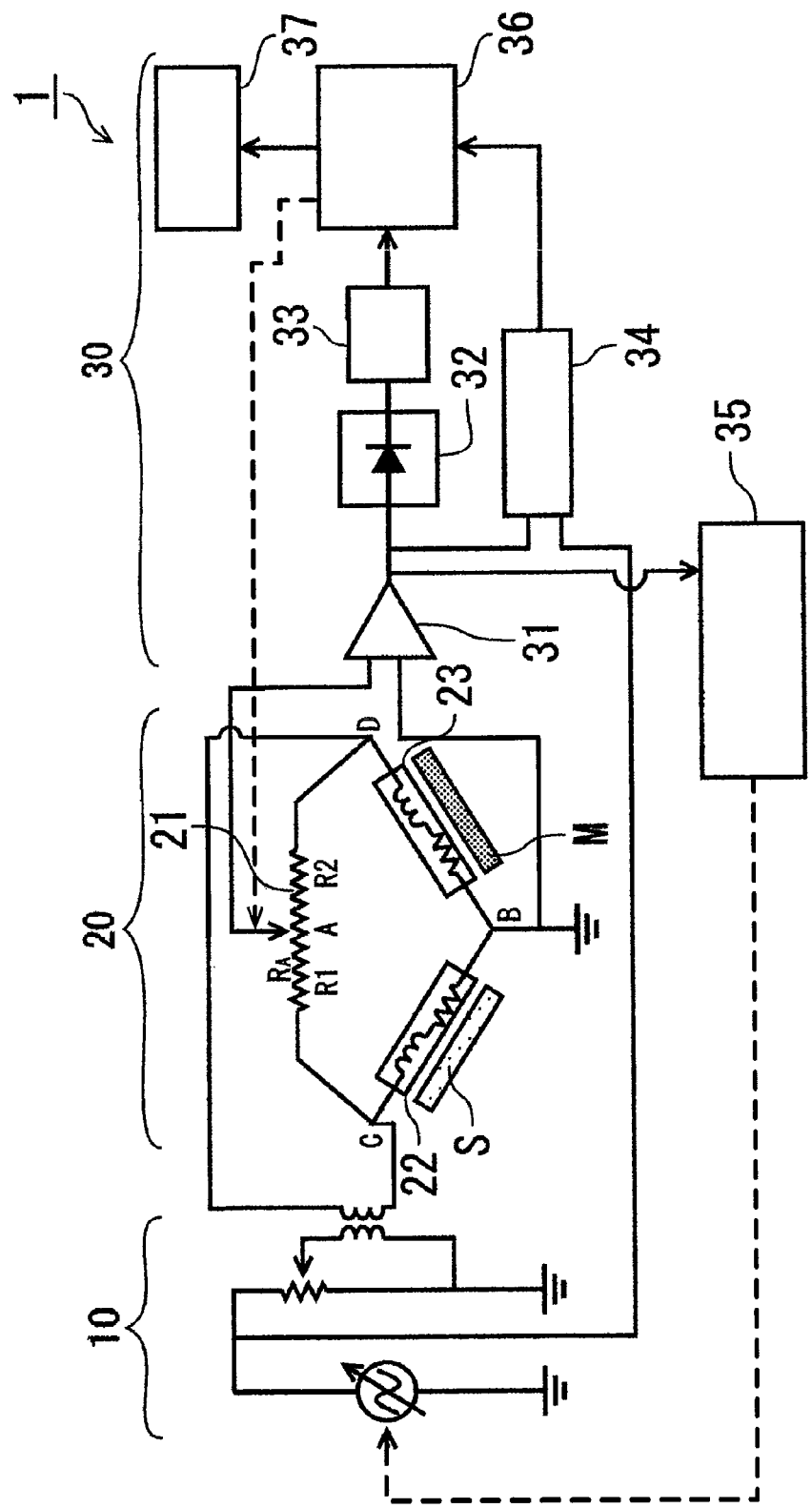
FIG. 5: An explanatory figure showing a variant example of the circuit configuration in a surface property inspection device according to an alternative embodiment of the present invention.

As shown in FIG. 5, a circuit configuration may be adopted for the AC bridge circuit 20 in which the amplifier 31 is connected to point A and point B, and the AC power supply 10 is connected to point C and point D.

The variable resistor setting step S2 is capable of perform adjustments in a state whereby two benchmark samples S are respectively brought into contact with the benchmark detector 22 and the inspection detector 23. By this method, as well, there are cases in which detection sensitivity is increased by adjusting the split ratio γ of the variable resistor 21 so that the voltage amplified output from the AC bridge circuit 20 or the voltage output from the LPF 33 are increased. For the variable resistor 21, it is desirable to set the split ratio γ to increase detection sensitivity according to the type of sample to be inspected, type of surface treatment, etc. when a benchmark sample S or reference sample is in contact with the inspection detector 23.

When inspection condition judgment step S8 is not executed, the surface property inspection device 1 may omit the phase comparator 34. The phase comparator 34, frequency adjustment device 35, or display means 37 may also be integrally disposed, such as by building them into the judgment means 36.

When the output of the AC bridge circuit 20 is sufficiently high during measurement of the sample under inspection M, the variable resistor setting step S2 or frequency setting step S3 may be omitted. When the frequency setting step S3 is omitted, the surface property inspection device 1 may omit the frequency adjustment device 35.

So long as the benchmark detector 22 and inspection detector 23 are capable of detecting magnetic changes associated with changes in surface treatment condition at a high accuracy, various types of detectors may be adopted.

The magnetic sensor 40 core 41 may be constituted to be capable of making contact along the surface shape of the sample under inspection M. For example, if the external shape of the sample under inspection M is cylindrical, the part of the core 41 contacting the sample under inspection M may be shaped to follow a cylindrical surface. This enables sufficient contact surface area to be assured between the core 41 and the sample under inspection M, and to prevent attenuation and leakage of magnetism between the sample under inspection and the magnetic sensor.

Effect of the Embodiment

In the surface property inspection device 1 according to an embodiment of the present invention, the AC bridge circuit 20 is furnished with a variable resistor 21 in which split ratio γ is variable, a benchmark detector 22 for detecting the magnetic properties of a benchmark sample S with a guaranteed good surface treatment condition, and an inspection detector 23 for detecting magnetic properties of a sample under inspection M for which the determination of surface treatment condition pass/fail is to be made. The AC bridge circuit 20 is constituted as a bridge circuit in a state of disequilibrium by resistor R1, resistor R2, benchmark detector 22, and inspection detector 23.

Using the surface property inspection device 1 and surface property inspection method of the present invention, the quality of the surface treatment condition of the sample under inspection M is judged by the judgment device 30 based on the voltage value output from the AC bridge circuit 20, therefore the surface treatment condition of the sample under inspection M can be inspected in the same measurement environment while constantly comparing to the benchmark sample S, thus enabling a highly accurate inspection of surface treatment condition using a simple circuit configuration.

By adopting the AC bridge circuit 20 configuration, it is unnecessary to correct for temperature, obtain test data according to the material of the sample under inspection, or calibrate device output relative to residual stress distribution, etc. Also, since the split ratio γ of the variable resistor and the frequency of the AC power supply 10 are variable, the circuit does not have to be redesigned even if the impedance of the benchmark detector 22 or the inspection detector 23 changes.

Also, by constituting two sides of the AC bridge circuit 20 as a variable resistor 21 with a variable split ratio γ, the split ratio is adjusted so that the output from the AC bridge circuit 20 is maximized and set to enable inspection under optimal conditions, thus permitting an expansion of the range of types of inspected piece and surface treatment inspectable with the surface property inspection device 1, and providing a device with a high degree of general purpose application, capable of handling multiple types of detectors.

By using the frequency adjustment device 35 to change the frequency of the AC power supplied to the AC bridge circuit 20 and set the frequency at which the amplitude of the voltage output from the AC bridge circuit 20 is maximized, the frequency at which the output from the AC bridge circuit 20 increases can be set by a single operation in response to samples under inspection M in which the surface treatment condition or shape differ so that impedance differs. Output therefore responds sensitively to changes in surface treatment condition, and inspection sensitivity can be improved.

Based on the above, a surface property inspection device 1 and surface property inspection method can be achieved with which the surface treatment condition of treated material such as steel subjected to surface treatments such as shot-peening treatment or heat treatment, nitriding, and the like can be non-destructively and precisely inspected, in a form offering a high degree of general purpose application.

The invention claimed is:

1. A surface property inspection device, comprising:
an AC bridge circuit;
an AC power supply for supplying AC power to the AC bridge circuit; and
a judgment device for making a pass/fail judgment of the surface treatment condition of a sample under inspection based on the output signal from the AC bridge circuit;

wherein the AC bridge circuit includes a variable resistor constituted so that the split ratio between a first resistor and a second resistor is variable, a benchmark detector having a first magnetic sensor for detecting the magnetic properties of a benchmark sample in a good surface treatment condition, and an inspection detector having a second magnetic sensor for detecting the magnetic properties of a sample under inspection for which a pass/fail inspection of the surface treatment condition is to be made; and the first resistor, the second resistor, the benchmark detector, and the inspection detector constitute a bridge circuit; and wherein the judgment device judges the pass/fail status of the surface treatment condition of the sample under inspection based on the output signal from the AC bridge circuit in a state in which AC power is supplied to the AC bridge circuit, the first magnetic sensor detects the magnetic properties of the benchmark sample, and the second magnetic sensor detects the magnetic properties of the sample under inspection.

2. The surface property inspection device according to claim 1, further comprising a frequency adjuster for adjusting and setting the frequency of AC power supplied from the AC power supply.

3. The surface property inspection device according to claim 2, wherein in a state in which the first magnetic sensor detects the magnetic properties of the benchmark sample, and the second magnetic sensor detects the magnetic properties of a non-surface treated sample or a reference sample which is a sample in a poor surface treatment condition, the frequency is set by the frequency adjuster so that the amplitude of the output signal from the AC bridge circuit increases.

4. The surface property inspection device according to claim 3, wherein in a state in which the first magnetic sensor detects the magnetic properties of the benchmark sample, and the second magnetic sensor detects the magnetic properties of a non-surface treated sample or a reference sample which is a sample in a poor surface treatment condition, the split ratio of the variable resistor is set so that the amplitude of the output signal from the AC bridge circuit increases.

5. The surface property inspection device according to claim 4, further comprising a phase comparator for detecting the phase difference between the AC power waveform supplied from the AC power supply and the output signal waveform from the AC bridge circuit, and wherein the judgment device makes a pass/fail judgment as to whether the inspection is being favorably conducted, based on the phase difference detected by the phase comparator.

6. The surface property inspection device according to claim 5, wherein the first and second magnetic sensors respectively comprise a core formed of a magnetic body and a coil wound on this core, and the second magnetic sensor detects the electromagnetic properties of the sample under inspection by supplying AC power from the AC power supply to the coil to form a closed magnetic path to the core and the surface of the sample under inspection.

7. The surface property inspection device according to claim 6, further comprising a sample under inspection placement device for adjusting the location and pressure load at which the sample under inspection is brought into contact with the second magnetic sensor.

8. A surface property inspection method, comprising steps of:
a preparation step for providing an AC bridge circuit and an AC power supply for supplying AC power to the AC bridge circuit; the AC bridge circuit comprising a variable resistor constituted so that the split ratio between a first resistor and a second resistor is variable, a benchmark detector including a first magnetic sensor for detecting the magnetic properties of a benchmark sample in a good surface treatment condition, and an inspection detector including a second magnetic sensor for detecting the magnetic properties of a sample under inspection for which a pass/fail determination of surface treatment condition is to be made, and the first resistor, the second resistor, the benchmark detector and the inspection detector constituting a bridge circuit;

a sample placement step for placing the benchmark sample in contact or proximity with the first magnetic sensor and for placing the sample under inspection in contact or proximity with the second magnetic sensor so that magnetic properties are detected;

an AC supply step for supplying AC power to the AC bridge circuit from the AC power supply; and a pass/fail judgment step for making a pass/fail judgment of the surface treatment condition of the sample under inspection based on an output signal output from the AC bridge circuit.

9. The surface property inspection method according to claim 8, further comprising a frequency setting step for setting the frequency so that the amplitude of the signal output from the AC bridge circuit increases when the frequency of the AC power supplied from the AC power supply is varied, in a state in which the first magnetic sensor detects magnetic properties of the benchmark sample and the second magnetic sensor detects magnetic properties of a non-surface treated sample, or of a reference sample which is a sample in a poor surface treatment condition; and in the AC supply step, AC power is supplied at the frequency set in the frequency setting step.

10. The surface property inspection method according to claim 9, further comprising a variable resistor setting step for determining a split ratio by adjusting the variable resistor so that output is increased, in a state in which the first magnetic sensor detects magnetic properties of the benchmark sample and the second magnetic sensor detects magnetic properties of a non-surface treated sample, or of a reference sample which is a sample in a poor surface treatment condition; and in the AC supply step, the variable resistor is set to achieve the split ratio determined in the variable resistor setting step.

11. The surface property inspection method according to claim 10, further comprising a threshold setting step for determining a threshold value for making a pass/fail judgment based on the output signal from the AC bridge circuit in a state in which the first magnetic sensor detects magnetic properties of the benchmark sample and the second magnetic sensor detects magnetic properties of a non-surface treated sample or of a reference sample which is a sample in a poor surface treatment condition, and based on the output signal from the AC bridge circuit in a state in which the first and second magnetic sensors respectively detect magnetic properties of the benchmark sample; and in the pass/fail judgment step, a pass/fail judgment of the surface treatment condition of the sample under inspection is made based on the threshold value.

12. The surface property inspection method according to claim 11, further comprising an inspection state judgment step for detecting phase differences between the AC power waveform supplied from the AC power supply and the AC bridge circuit output signal waveform to make a pass/fail judgment of the inspection state based on detected phase differences.

13. The surface property inspection method according to claim 12, wherein the first and second magnetic sensors respectively comprise a core formed of a magnetic body and a coil wound on this core, and the second magnetic sensor detects the electromagnetic properties of the sample under inspection by supplying AC power from the AC power supply to the coil to form a closed magnetic path to the core and the surface of the sample under inspection.

14. The surface property inspection method according to claim 13, wherein in the sample placement step the pressure load for bringing the first magnetic sensor into contact with the benchmark sample and the pressure load for bringing the second magnetic sensor into contact with the sample under inspection are set to be approximately the same.

* * * * *